United States Patent
Schröder et al.

(10) Patent No.: US 9,732,056 B2
(45) Date of Patent: *Aug. 15, 2017

(54) 2-(ALKOXY OR ARYLOXY CARBONYL)-4-METHYL-6-(2,6,6-TRIMETHYLCYCLOHEX-1-ENYL)HEX-2-ENOIC ACID COMPOUNDS, ITS PREPARATION AND USE

(71) Applicant: Givaudan, S.A., Vernier (CH)

(72) Inventors: Fridtjof Schröder, Hettlingen (CH); Urs Mueller, ThaMuang (TH); Jurg Daniel Oetiker, Mannedorf (CH)

(73) Assignee: Givaudan, S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/854,705

(22) Filed: Sep. 15, 2015

(65) Prior Publication Data

US 2016/0002192 A1    Jan. 7, 2016

Related U.S. Application Data

(62) Division of application No. 14/563,312, filed on Dec. 8, 2014, now Pat. No. 9,163,000, which is a division of application No. 13/995,368, filed as application No. PCT/EP2011/073550 on Dec. 21, 2011, now Pat. No. 8,933,253.

(30) Foreign Application Priority Data

Dec. 21, 2010 (GB) .................. 1021584.6

(51) Int. Cl.
| | |
|---|---|
| *C07C 403/20* | (2006.01) |
| *C07C 69/608* | (2006.01) |
| *C07C 51/38* | (2006.01) |
| *C07C 57/26* | (2006.01) |
| *C07C 67/475* | (2006.01) |
| *C07C 67/32* | (2006.01) |
| *C07D 307/92* | (2006.01) |

(52) U.S. Cl.
CPC ......... *C07D 307/92* (2013.01); *C07C 51/38* (2013.01); *C07C 57/26* (2013.01); *C07C 67/32* (2013.01); *C07C 67/475* (2013.01); *C07C 69/608* (2013.01); *C07C 403/20* (2013.01); *C07C 2101/16* (2013.01); *C07C 2102/48* (2013.01)

(58) Field of Classification Search
CPC ..... C07C 403/20; C07C 69/608; C07C 51/38; C07C 57/26; C07D 307/92; C07C 67/475; C07C 67/32
See application file for complete search history.

(56) References Cited

U.S. PATENT DOCUMENTS

| | | | |
|---|---|---|---|
| 4,503,240 A | 3/1985 | Staiger et al. | |
| 5,292,902 A | 3/1994 | Helmlinger | |
| 8,765,980 B2 * | 7/2014 | Schroder | C07C 67/32 549/458 |
| 2008/0064886 A1 | 3/2008 | Frater et al. | |
| 2010/0168462 A1 | 7/2010 | Mimoun et al. | |

FOREIGN PATENT DOCUMENTS

| | | |
|---|---|---|
| DE | 32 40 054 A1 | 5/1984 |
| EP | 0 165 458 A2 | 12/1985 |
| EP | 0 525 579 A2 | 2/1993 |
| EP | 0 550 889 A1 | 7/1993 |
| WO | WO 2006/010287 A1 | 2/2006 |
| WO | WO 2007/096791 A1 | 8/2007 |

OTHER PUBLICATIONS

PCT/EP2011/073550—International Search Report, Apr. 26, 2012.
PCT/EP2011/073550—International Written Opinion, Apr. 26, 2012.
PCT/EP2011/073550—International Preliminary Report on Patentability, Jun. 25, 2013.
GB 1021584.6—Great Britain Search Report, Mar. 25, 2011.
Breit, et al., "Combined Transition-Metal- and Organocatalysis: An Atom Economic C3 Homologation of Alkenes to Carbonyl and Carboxylic Compounds", Chemistry—a European Journal, Mar. 15, 2010, pp. 3423-3433, vol. 16 (11), Abstract Only.
Ley, et al., "New Tools for Molecule Makers: Emerging Technologies", Systems Chemistry, Bozen, Italy, Mar. 16, 2009.

(Continued)

*Primary Examiner* — Sun Jae Yoo
(74) *Attorney, Agent, or Firm* — Curatolo Sidoti Co., LPA; Joseph G. Curatolo; Salvatore A. Sidoti

(57) ABSTRACT

Compounds of the formula 1

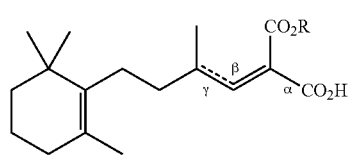

wherein, R is hydrogen, alkyl or substituted alkyl, aryl or substituted aryl, are useful intermediates in the synthesis of fragrance ingredients such as Ambrox 2

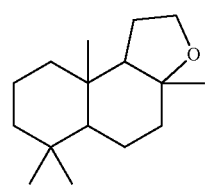

2 Claims, No Drawings

(56) References Cited

OTHER PUBLICATIONS

Flipo, et al., "Novel Selective Inhibitors of the Zinc Plasmodial Aminopeptidase PfA-M1 as Potential Antimalarial Agents", Journal Medical Chemistry, vol. 50, Feb. 28, 2007, pp. 1322-1334.

Lucius, "Cyclisation Homologer Sesquiterpensäuren", Agnew. Chem., No. 7, 1956, pp. 247.

Intellectual Property Office of Singapore Written Opinion, issued Apr. 28, 2014 for corresponding Singapore Patent Application No. 201303903-7.

Intellectual Property Office of Singapore Written Opinion issued Feb. 13, 2015 for corresponding Singapore Patent Application No. 201303903-7.

G. Lucius, Cyclisation Homologer Sesquiterpensäuren II. Konfiguration Der Totalsynthetishen Stereoisomeren dl-Laktone. *Archie Der Pharmazie*, Feb. 2, 1958, vol. 291, No. 63, pp. 57-66.

\* cited by examiner

2-(ALKOXY OR ARYLOXY CARBONYL)-4-METHYL-6-(2,6,6-TRIMETHYLCYCLOHEX-1-ENYL)HEX-2-ENOIC ACID COMPOUNDS, ITS PREPARATION AND USE

The present application is a divisional application of co-pending U.S. Ser. No. 14/563,312, filed Dec. 8, 2014, which is a divisional application of U.S. Ser. No. 13/995,368, having a 35 USC 371 (c) date of Nov. 27, 2013, now U.S. Pat. No. 8,933,253, which is a national stage application of International Application No. PCT/EP2011/73550, filed 21 Dec. 2011, which claims the benefit of Great Britain Application No. 1021584.6, filed 21 Dec. 2010, which applications are incorporated herein by reference.

The invention is concerned with organic compounds their preparation and use as intermediates in the synthesis of fragrance ingredients.

Many fragrance ingredients that are used by perfumers in the creation of new and exciting fragrance accords are commodity ingredients, that is, they are non-proprietary and versions of the ingredients, which may differ in price and quality, and are available from many different suppliers. The uptake of a particular version of such ingredients by perfumers may be based on considerations of costs as well as on performance.

3a,6,6,9a-tetramethyldodecahydronaphtho[2,1-b]furan 2, from which certain isomers or isomer mixtures are on the market, for example Ambrofix® (Givaudan), Ambroxan® (Kao), Cetalox® and Fixambrene® (both Firmenich) is an example of such a commodity fragrance ingredient.

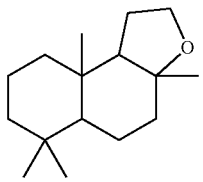

2

There remains a need to provide novel key intermediates and novel syntheses that enable key fragrance ingredients to be produced in high purity, good yield and in a cost-effective manner.

The invention provides in a first aspect a compound of formula 1

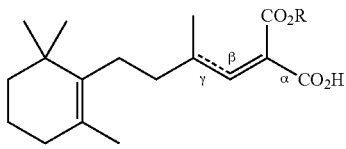

1 wherein, R is hydrogen, alkyl or substituted alkyl, aryl or substituted aryl, more particularly R is hydrogen, methyl or ethyl.

The double bond in the side chain of compound 1 may be in the α,β-position (conjugated), or in the β,γ-position (unconjugated).

The applicant has found that compounds 1 are useful synthetic intermediates of fragrance ingredients such as 3a,6,6,9a-tetramethyldodecahydro-naphtho[2,1-b]furan 2, from which certain isomers or isomer mixtures are on the market, for example Ambrofix® (Givaudan), Ambroxan® (Kao), Cetalox® and Fixambrene® (both Firmenich).

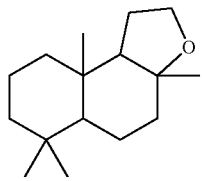

2

Syntheses of compound 2 are well known in the art. The transformation of conjugated malonates 3 (R=alkyl) to E configured β,γ-unsaturated esters 4 is described in WO 2007096791 (Firmenich). Therein, said transformation is claimed to be catalyzed by salts of the formula $MX_n$ (with M being a metal of groups I, II and III, and X an anion of an acid HX) in stoichiometric amounts of an organic acid, as shown in the scheme below. The esters 4 are key intermediates in the synthesis of the important fragrance compound 2.

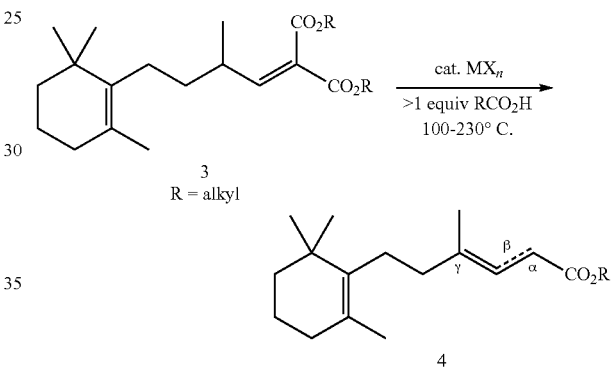

However, α,β-unsaturated malonic acids, of which the compounds of formula 1 are examples, are generally considered as being less stable and more difficult to handle than the corresponding α,β-unsaturated malonates 3, e.g. during preparation, distillation, and/or under aqueous work-up conditions, which can make their preparation as well as further transformation to useful compounds troublesome. This might explain why the condensation of aldehyde 5 (see below for structure) with malonic acid has only produced acid 6 (for structure, see below) with poor E/Z (1:1) and α,β/β,γ ratios, (G.Lucius, Angew. Chem. 68, 247, 1956 or R. L. Snowdon, Siegfried Symposium, Universität Zürich, 2006).

Progress in this field has been recently reported by Breit et al. (Chem. Eur. J. 16, 3423, 2010). However, the unsaturated malonic acids produced by his method lack the γ-substituent, which would give, after decarboxylation, E/Z isomers in case of β,γ-unsaturation (apart from a much different α,β/β,γ-selectivity). Futhermore, this so-called "decarboxylative Knoevenagel reaction" needs stoichiometric amounts of nitrogen-containing bases (especially when unsaturated acids are addressed). This makes the process uneconomic on a larger scale, as large quantities of the (often expensive) N-containing bases (such as pyridine, DMAP, Lutidine or DBU) have to be recovered from the waste-waters.

Therefore, the findings that compound 1 is a useful intermediate for the preparation of valuable fragrance ingredients, and that it can be prepared economically is surprising.

Accordingly, the invention provides in another of its aspects the use of a compound of the formula 1 in the preparation of an ester 4 or the acid 6, by the decarboxylation of the compound of formula 1.

Starting from the compounds 1, the esters 4 can be prepared, which exhibit good β,γ/α,β and E/Z ratios, for example around 80:20 or higher, employing reagent systems used for the E-selective transformation of malonates 3 to esters 4 as described above. The good β,γ/α,β and E/Z ratios may be attributable to the free carboxylic acid group in compounds 1, which makes the overall reaction easier to achieve, because a transesterification step, required in WO 2007096791, is not necessary.

In a particular embodiment of the invention, decarboxylation of compound 1, is carried out at ambient temperature, which may be about 0 to 130 degrees, e.g. at 25° C. for the purpose of this invention. The reaction may be carried out in a solvent, or in a solvent-free system. If solvents are to be employed, it is preferred that they are polar aprotic solvents, for example DMF, N-alkyl-pyrrolidinones or dialkylsulfoxides more particularly DMSO. The reaction may proceed stereospecifically and without erosion of the E/Z ratio.

An example of this decarboxylation reaction is shown in the reaction scheme below wherein the compound 1a is decarboxylated in DMSO at ambient temperature, giving the corresponding methyl ester 4a. The ester 4a can be produced in this way stereospecifically and without erosion of the E/Z 72:28 ratio.

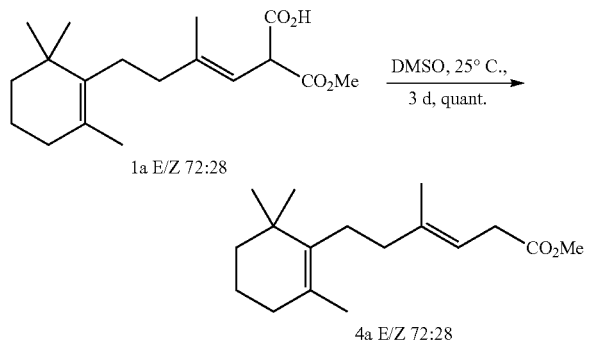

In another particular embodiment of the decarboxylation of compounds of the formula 1, the reaction proceeds thermally, e.g. between 50 and 350° C. under flow conditions, e.g. on a Gas Chromatography (GC) column. GC uses a gaseous flow but other flow conditions are contemplated, e.g. the continuous decarboxylation of a compound of the formula 1 dissolved in a solvent or solvent-free in a coil reactor. Appropriate flow reactors are known to the chemist experienced in flow and analytical techniques (see for example Ley, S. V.; Baxendale, I. R. "New Tools for Molecule Makers: Emerging Technologies", Proceedings of the Symposium "System Chemistry", Bozen, Italy, Mai 26-30, 2008, Beilstein Institute), which is hereby incorporated by reference.

A particular example of this reaction under flow conditions is shown in the reaction scheme below wherein the compound 1b (Z or E/Z 1:1) is converted to the ester of the formula 4a.

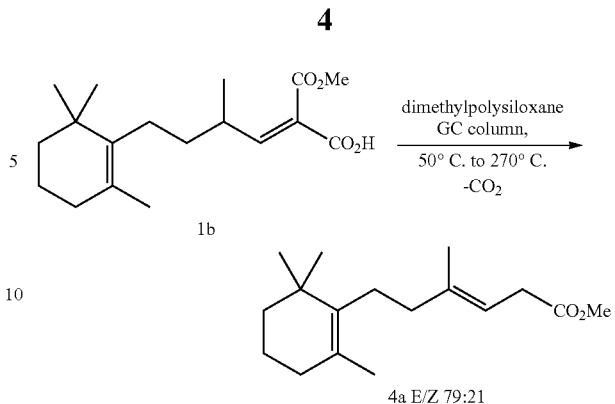

The ester 4a can be produced in this manner with good E/Z ratios, for example around 80:20.

In yet another particular embodiment of the decarboxylation of compounds of the formula 1, decarboxylation is carried out in the presence of a metal halide salt $MX_n$ (e.g. LiCl) in a polar aprotic solvent, e.g. N-methyl-pyrrolidone (NMP), to yield the corresponding deconjugated acid with high E/Z ratios.

A particular example of this decarboxylation reaction is shown in the reaction scheme below, in which compound 1c is decarboxylated in the presence of a salt $MX_n$ (e.g. LiCl) in a polar aprotic solvent (e.g. NMP), giving deconjugated acid 6 with high E/Z ratios (e.g. 86:14).

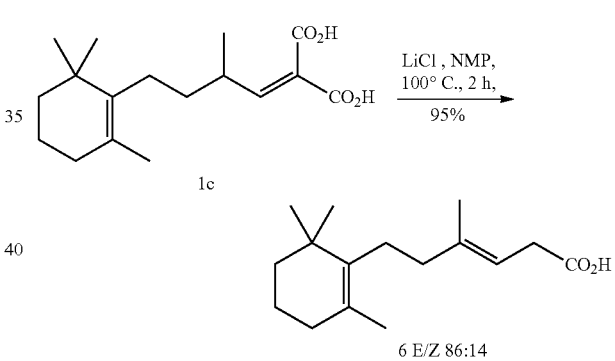

Therefore, the invention provides in another of its aspects, a process for the preparation of β,γ-unsaturated-γ,γ-disubstituted acids, e.g. the acid 6, said process comprising the step of reacting at a temperature of between about 50 to about 200, more particularly about 75 to about 125 degrees centigrade a conjugated malonic acid of the formula 1, e.g. the compound 1c with a salt $MX_n$, optionally in the presence of a polar solvent, wherein $MX_n$ is an inorganic salt or an organic cation/halide anion pair, X is a halide and n is an integer of 1 to 3, and M is a group I, II or III metal when $MX_n$ is an inorganic salt, or M is selected from the group consisting of pyridinium, piperidinium, pyrrolidinium, imidazolium, ammonium, phophonium and sulphonium, when $MX_n$ is an organic cation/halide anion pair. $MX_n$ can be an ionic liquid, and in such cases it can act as both salt and a solvent.

The reaction proceeds with good yield and with good E/Z selectivities up to 90:10 or even up to 95:5.

The esters of formula 4, and the acid 6 are both important intermediates into the compound 2 and its isomers. Particularly interesting isomers of compound 2 can be achieved when the side chain double bonds of ester 4 or acid 6 are in the β,γ-position with E configuration.

Methods for a 3-step transformation from an ester of formula 4 to Ambrox via bicyclic ester 7 are known in the art of fragrance chemistry, e.g. from WO 2006010287, which is hereby incorporated by reference. An example of this synthetic route is shown in the scheme below, wherein R is as hereinabove defined.

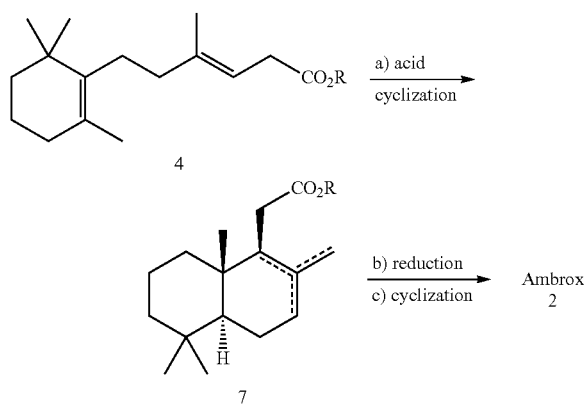

The transformation consists of a series of cyclisation and reduction steps, proceeding with a first cyclisation step, a reduction step, and finally a second cyclisation step.

The first and second cyclization steps proceed in the presence of an acid, as described more fully in WO2006010287, which is herein incorporated by reference. Examples of suitable cyclisation agents include mineral acids, organic acids and Lewis acids. Examples of suitable mineral acids include phosphoric acid, sulphuric acid and perchloric acids, heteropolyacids such as $H_3[P(W_3O_{10})_4]$, acid resins such as Dowex™ 50 or Amberlyst™. Examples of suitable protonic acids include hydrohalide acids such as hydrogen chloride and hydrogen bromide. Examples of organic acids include acetic acid, trifluoroacetic acid, methanesulphonic acid and chlorosulphonic acid. These named acids are purely exemplary. It is also possible to use mixtures of the abovementioned acids.

Non-restrictive examples of suitable Lewis acids include products such as $AlCl_3$, $TiCl_4$, $SnCl_4$ and $MeAlCl_2$.

The cyclisation steps may be carried out in an inert organic solvent. The selection of a suitable solvent is well known within the skill of the art, but suitable examples include petroleum ether, halogenated hydrocarbons such as chloroform, dichloromethane and trichloroethane, aromatic hydrocarbons such as benzene, toluene and nitrobenzene, ethers such as diethyl ether, methyl tert-butyl ether and tetrahydrofuran, esters, nitrogen containing hydrocarbons such as nitromethane, nitropropane and acetonitrile.

The reduction step b) may be carried out with a reducing agent. Any reducing agent that is capable performing the desired transformation may be used, and the skilled person will readily be able to identify a suitable reducing agent. Non-limiting examples of suitable reducing agents are hydride sources such as lithium aluminium hydride, sodium borohydride, Red-Al and silanes. The reduction is carried out in an inert solvent, the selection of which will be evident for a skilled person in the art.

E-Cyclohomofarnesic acid 6 is (as is the case with esters 4) another valuable precursor of Ambrox 2. The cyclization of 6 to Sclareolide 8 and further processing of this key intermediate (8) to Ambrox 2 has been described in numerous articles and patents known to the person skilled in the art, and (as in the case of compounds 4) the double bond of 6 should be preferably in the β,γ-position with E-configuration to access Sclareolide 8 and the olfactorily interesting isomers of Ambrox 2 with good selectivity, for example about 90% or greater.

These transformations can be performed substantially as described above in relation to esters 4, or according to methods described in EP 525579, EP 5500889, EP 165458 and DE 3240054, all of which citations are incorporated herein by reference.

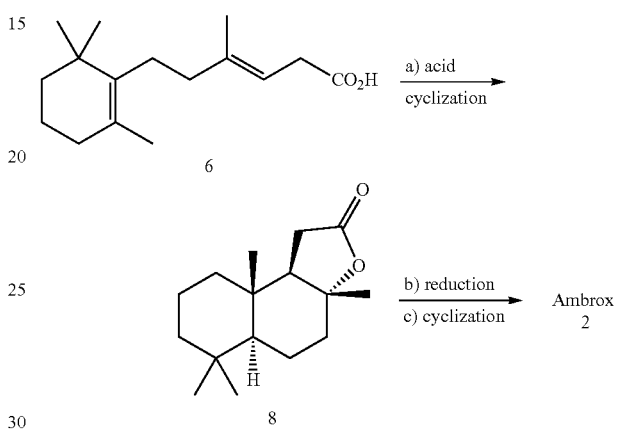

The compounds 1 can be formed in a quite straightforward fashion by the hydrolysis of the corresponding conjugated malonate 3.

In an example of the synthesis of compounds of the formula 1, compound 1a (double bond in the β,γ-position and R=Me) is obtained from compound 3a, which is hydrolysed enzymatically using Pig Liver Esterase (PLE) as is shown in the reaction scheme below.

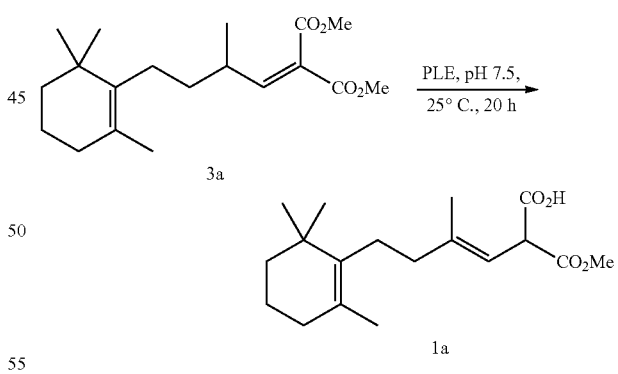

In another example of the synthesis of compounds of the formula 1, compound 1b may be prepared by mono-hydrolysis of conjugated methyl malonate 3a in protic solvents, for example water and alcohols ROH or mixtures of both, with ROH including monoalcohols, diols and triols and R being any organic residue, which may be branched or unbranched, e.g. methyl or ethyl, and in the presence of a base, such as hydroxides of alkali and/or earth alkali or group III metals. For example conjugated Meldrum's acid 3b is treated with KOH in methanol (see the reaction scheme below) to give half-malonate 1b:

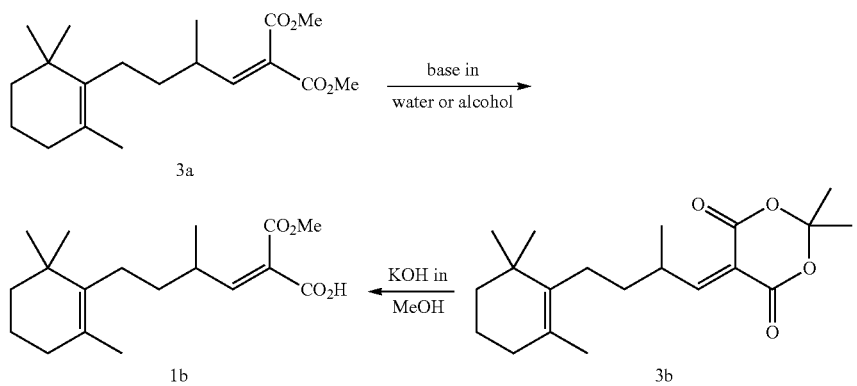

In yet another example of the synthesis of a compound of the formula 1, compound 1c can be prepared by condensation of aldehyde 5 with malonic acid. This transformation

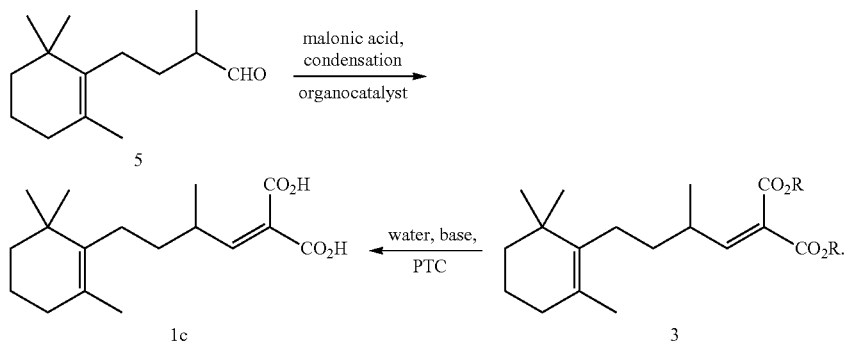

can be carried out with organocatalysts or ionic liquids or mixtures of both, used in catalytic or stoichiometric amounts, but catalytic amounts are preferred. The term organocatalyst is well known in the art. Preferred organocatalysts according to the invention comprise an amino and an acid function. These functions can be linked covalently in the same molecule, such as in proline and other amino acids, or such as in glycylglycine (H-Gly-Gly-OH, 2-(2-aminoacetamido)acetic acid) and other peptides. The amine component and the acid component can be mixed before or during the condensation reaction to form an ammonium carboxylate salt. In these salts the carboxylate is derived from carboxylic or polycarboxylic acids such as acetic acid, malonic acid or citric acid. The amine component is derived from ammonia, a primary, a secondary amine or a polyamine Secondary amines are preferred, e.g. piperidine, piperazine, pyrrolidine and morpholine. The organocatalysts are used in a solvent or solvent systems which form azeotropes with water such as cyclohexane, benzene, toluene, iso-propanol or tert-butanol. Azeotropes with boiling points of around 70-90° C. are preferred as condensation reactions using such azeotropes proceed and water is removed without uncontrolled decarboxylation of malonic acid or condensation product 1c. Under these conditions relatively low amounts of 1-1.2 equiv of malonic acid are sufficient for complete conversion of aldehyde 5 to acid 1c.

In yet another example of the synthesis of a compound 1, compound 1c can be prepared by hydrolysis of conjugated malonate 3 with inorganic base in water and in the presence of phase transfer catalysts (PTC) such as 18-crown-6 or tetraethylammonium chloride (TEBAC) under reflux.

The starting materials 3a, 3b and 5 are all commonly available reagents or can be derived from commonly available starting materials according to methods well known in the art. A more detailed discussion of the starting materials and syntheses is set out in the Examples, below.

It has also been found, that it is not necessary to work-up and isolate compound 1c after condensation of malonic acid with aldehyde 5, because the compound 1c can be decarboxylated in-situ to cyclohomofarnesic acid 6 giving the same good yield and E/Z ratio as from isolated 1c. An example of this in-situ reaction is shown in the reaction scheme below:

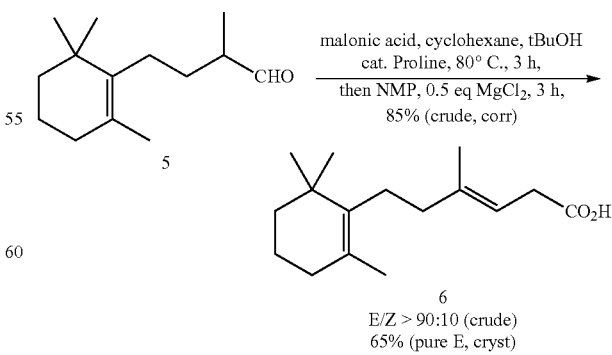

Said process represents a significant advantage over previous syntheses of E-Cyclohomofarnesic acid 6, as it allows its efficient one-pot preparation from aldehyde 5 with good yield and purity, using relatively low amounts of inexpensive catalysts, reagents and solvents, which can be recycled.

The invention is further described with reference to the following examples.

EXAMPLE 1

Dimethyl 2-(2-methyl-4-(2,6,6-trimethylcyclohex-1-enyl)butylidene)malonate 3a

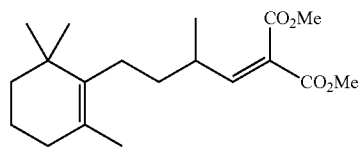 [SMILES: COC(=O)C(=CC(C)CCC1=C(C)CCCC1(C)C)C(=O)OC]

Under water-free conditions titanium(IV) chloride (91 g, 0.5 mol) in tetrachloromethane (120 ml) are added dropwise within 45 min to tetrahydrofuran at 0° C. The mixture is stirred for another 30 min at this temperature, then 2-Methyl-4-(2,6,6-trimethylcyclohex-1-enyl)butanal 5 (50 g, 0.24 mol) (M. Matsui et al., *Agric. Biol. Chem.* 50, 1475-1480, 1986) and dimethyl malonate (31.7 g, 0.24 mol) in tetrahydrofuran (50 ml) are added within 15 min at 0° C. followed by dropwise addition of pyridine (76 g) in tetrahydrofuran (240 ml) over 90 min at 0° C. The orange-brown suspension is stirred for 18 h at 25° C., then poured upon ice/water and extracted with tert-butyl methyl ether. The combined organic layers are washed with water and conc. NaCl and dried over MgSO$_4$. After filtration and evaporation of the solvents the crude product (75 g) is short-path-distilled giving 62.5 g 3a at 170° C./0.07 mbar (81% yield, purity>98%). Analytical data: $^1$H-NMR (400 MHz, CDCl$_3$): δ 0.95 (s, 6H), 1.1 (d, 3H), 1.4-1.5 (4H), 1.5-1.6 (2H), 1.58 (s, 3H), 1.8-2.0 (2H), 2.5 (m, 1H), 3.8 (s, 3H), 3.85 (s, 3H), 6.85 (d, 1H) ppm. $^{13}$C-NMR (400 MHz, CDCl$_3$): δ 19.45 (t), 19.55 (q), 19.75 (q), 26.4 (t), 28.5 (q), 32.7 (t), 34.8 (s), 35.7 (d), 36.8 (t), 39.7 (t), 52.1 (q), 52.2 (q), 126.7 (s), 127.1 (s), 136.8 (s), 154.9 (d), 164.4 (s), 166.0 (s). MS (EI): m/z (%) 322 (M$^+$, 10), 307 ([M-15]$^+$2), 275 (6), 259 (7), 243 (16), 215 (11), 200 (18), 187 (19), 175 (20), 173 (16), 172 (100), 153 (22), 145 (28), 140 (70), 137 (27), 135 (34), 123 (60), 122 (28), 121 (42), 109 (35), 108 (34), 95 (62), 93 (36), 81 (44), 79 (33), 55 (36), 41 (35). IR (film): 2950 (m), 2926 (m), 2865 (m), 1725 (s), 1642 (w), 1454 (w), 1433 (m), 1363 (w), 1327 (w), 1246 (s), 1221 (s), 1204 (s), 1168 (w), 1104 (w), 1054 (m), 991 (w), 945 (w), 925 (w), 833 (w), 762 (w).

EXAMPLE 2

2,2-Dimethyl-5-(2-methyl-4-(2,6,6-trimethylcyclohex-1-enyl)butylidene)-1,3-dioxane-4,6-dione 3b

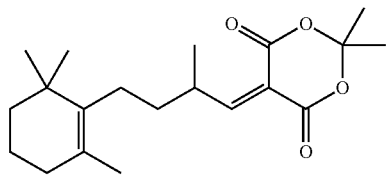 [SMILES: CC1=C(CCC(C)C=C2C(=O)OC(C)(C)OC2=O)C(C)(C)CCC1]

Under stirring and nitrogen first L-prolin (0.26 g, 2.2 mmol), then 2-Methyl-4-(2,6,6-trimethylcyclohex-1-enyl)butanal 5 (10 g, 45 mmol) (M. Matsui et al., *Agric. Biol. Chem.* 50, 1475-1480, 1986) are added to 2,2-dimethyl-1,3-dioxane-4,6-dione (6.65 g, 45 mmol) in acetonitrile (100 ml) at 25° C. After 90 h at this temperature the solvent is stripped off under reduced pressure. Tert-butyl methyl ether and 2 M HCl are added to the residue. Phase separation, extraction of the aqueous phase with tert-butyl methyl ether, washing of the combined organic phase with water, conc. NaHCO$_3$ and water, drying over MgSO$_4$, filtration and evaporation under reduced pressure gives 16 g of an oily residue. Flash chromatography over Silicagel (hexane/tert-butyl methyl ether 9:1) and evaporation of the solvents gives 0.8 g (8%) of aldehyde 5 and 12.8 g (87%) of 3b as colorless oils. Analytical data: $^1$H-NMR (400 MHz, CDCl$_3$): δ 0.95 (s, 6H), 1.15 (d, 3H), 1.4 (3H), 1.5-1.6 (3H), 1.55 (s, 3H), 1.75 (s, 6H), 1.85-1.9 (3H), 2.05 (m, 1H), 3.7 (m, 1H), 3.85 (s, 3H), 7.7 (d, 1H) ppm. $^{13}$C-NMR (400 MHz, CDCl$_3$): δ 19.0 (q), 19.4 (t), 19.8 (q), 26.6 (t), 27.6 (2 q), 28.5 (q), 28.6 (q), 32.7 (t), 34.8 (s), 35.7 (d), 36.9 (t), 39.7 (t), 104.7 (s), 117.1 (s), 127.6 (s), 136.5 (s), 159.8 (s), 162.0 (s), 172.9 (d). MS (DIP, EI): m/z (%) 334 (M$^+$, 4), 227 (26), 276 (79), 261 (12), 259 (47), 258 (100), 248 (72), 243 (81), 233 (28), 230 (21), 220 (26), 215 (34), 202 (41), 189 (31), 187 (24), 175 (28), 150 (55), 137 (19), 135 (71), 123 (31), 122 (33), 121 (26), 107 (17), 95 (16). IR (film): 2930 (m), 2866 (m), 1736 (s), 1624 (m), 1455 (w), 1367 (m), 1276 (s), 1201 (s), 1014 (m), 924 (m), 800 (m).

EXAMPLE 3

(E)-2-(Methoxycarbonyl)-4-methyl-6-(2,6,6-trimethylcyclohex-1-enyl)hex-3-enoic acid 1a

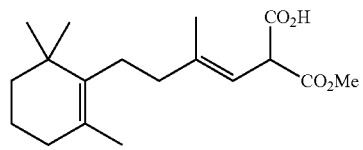 [SMILES: COC(=O)C(/C=C(\C)CCC1=C(C)CCCC1(C)C)C(=O)O]

Conjugated malonate 3a (0.5 g, 1.5 mmol, from a 5% stock solution in methanol) was incubated with 375 Units Pig Liver Esterase (Sigma-Aldrich) in 100 mM potassium phosphate buffer pH 7.5, at 25° C. and with constant stirring. After 20 h of incubation the pH of the reaction mixture was set to 9 with 30% NaOH followed by incubation at room temperature for 30 min with constant stirring. The reaction mixture was then extracted 3 times with 250 ml tert-butyl methyl ether. The organic phase was washed twice with 125 ml deionized water and once with saturated NaCl solution, dried over Na$_2$SO$_4$ and finally evaporated under reduced pressure at 45° C. 0.4 g of conjugated malonate 3a were recovered. The pH of the aqueous phase left from the basic (pH 9) extraction was set to 3 with conc. HCl. Extraction with tert-butyl methyl ether, washing with water and saturated NaCl, drying over Na$_2$SO$_4$, filtration and evaporation under reduced pressure at 45° C. gave 62 mg (13%) of deconjugated half malonate 1a as colorless oil and E/Z 72:28 according to NMR. The suppression of byproduct 1b depends on the quality of the PLE employed, with aged PLE (>1 year) giving exclusively isomer 1a. Analytical data of the E-isomer: $^1$H-NMR (400 MHz, CDCl$_3$): δ 0.96 (s, 6H), 1.56 (3H), 1.67 (s, 3H), 1.4 (2H), 1.5 (2H), 1.9 (2H), 2.0

(4H), 3.6 (s, 3H, OMe), 4.2 (d, 1H), 5.4 (d, 1H) ppm. $^{13}$C-NMR (400 MHz, CDCl$_3$): δ 16.4 (q), 19.1 (t), 19.6 (q), 27.2 (t), 28.4 (2 q), 32.3 (t), 34.6 (s), 39.3 (t), 39.7 (t), 50.9 (d), 52.2 (q), 116.3 (d), 126.8 (s), 136.3 (s), 141.0 (s), 169.1 (s), 169.6 (s). Configuration of the E/Z isomers determined by NMR-analysis on a freshly prepared solution of 1a in DMSO-D$_6$: COSY, HSQC, HMBC and NOESY.

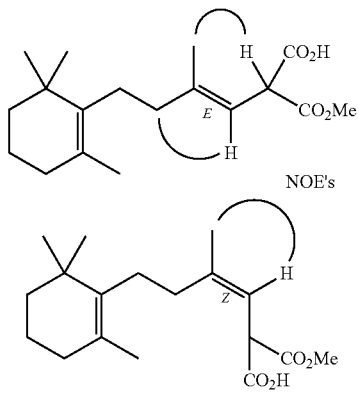

EXAMPLE 4

2-(Methoxycarbonyl)-4-methyl-6-(2,6,6-trimethylcyclohex-1-enyl)hex-2-enoic acid 1b

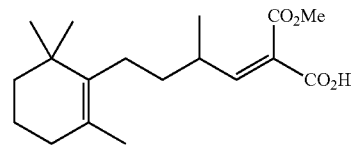 [SMILES: COC(=O)/C(=C\C(C)CCC1=C(C)CCCC1(C)C)C(=O)O]

Conjugated malonate 3a (10 g, 29.5 mmol) in THF (130 ml) is vigorously stirred with NaOH (4.8 g, 118 mmol) in water (120 ml) at 25° C. for 5 h. After addition of conc. NaHCO$_3$ the mixture is extracted with tert-butyl methyl ether. The organic phase, which contains aldehyde 5, is discarded. The water phase is acidified with conc. HCl to pH 2 and extracted with tert-butyl methyl ether. The organic phase is dried over MgSO$_4$, filtered and evaporated under reduced pressure giving 7.5 g (82%) of crude 1b with Z-configuration, which isomerizes upon standing slowly to an E/Z 1:1 mixture. Analytical data of the Z-isomer: $^1$H-NMR (400 MHz, CDCl$_3$): δ 0.96 (s, 6H), 1.1 (d, 3H), 1.4-1.6 (6H), 1.56 (s, 3H), 1.85-2.0 (4H), 3.8 (m, 1H), 3.9 (s, 3H), 7.2 (d, 1H) ppm. $^{13}$C-NMR (400 MHz, CDCl$_3$): δ 19.41 (t), 19.42 (q), 19.8 (q), 26.4 (t), 28.56 (q), 28.57 (q), 32.7 (t), 34.8 (s), 36.0 (d), 36.8 (t), 39.7 (t), 52.6 (t), 124.0 (s), 127.3 (s), 136.7 (s), 161.0 (d), 166.6 (s), 167.3 (s). Z-Configuration determined on freshly prepared 1b by non-decoupled $^{13}$C-NMR-(method described in *J. Med. Chem.* 50, 1322-1334, 2007), HSQC- and HMBC-analysis in DMSO-D$_6$. MS (DIP, EI): m/z (%) 308 (M$^+$, 65), 290 (10), 275 (20), 259 (24), 243 (76), 215 (29), 190 (27), 175 (32), 158 (100), 140 (43), 123 (29), 121 (22).

EXAMPLE 5

Alternative preparation of conjugated half-malonate 1b: Conjugated malonate 3a (10 g, 29 mmol) and KOH (1.9 g, 29 mmol) in dry methanol (60 ml) are stirred at 25° C. for 70 h. The mixture is diluted with water and extracted with tert-butyl methyl ether. The organic phase, which contains aldehyde 5, E-ester 4a and substrate 3a (4 g after evaporation of the solvents) is discarded. The aqueous phase is acidified to pH 2 and extracted with tert-butyl methyl ether, dried over MgSO$_4$, filtered and evaporated under reduced pressure to give 6.7 g (76%) of crude 1b with an E/Z ratio of 1:1 and analytical data identical to the ones obtained for the E/Z mixture in example 4.

EXAMPLE 6

Alternative preparation of conjugated half-malonate 1b from Meldrum's acid derivative 3b: Compound 3b (10 g, 28.5 mmol) in dry methanol (60 ml) containing KOH (1.9 g, 28.5 mmol) is stirred at 65° C. for 4 h. After cooling to 25° C. the mixture is diluted with water and extracted with tert-butyl methyl ether. The organic phase (1.5 g after evaporation of the solvents) is discarded. The aqueous phase is acidified to pH 2 and extracted with tert-butyl methyl ether, dried over MgSO$_4$, filtered and evaporated under reduced pressure to give 7.6 g (86%) of crude 1b as E/Z 1:1 mixture. The analytical data are identical to the ones obtained for the E/Z mixture in example 4.

EXAMPLE 7

2-(2-Methyl-4-(2,6,6-trimethylcyclohex-1-enyl)butylidene)malonic acid 1c

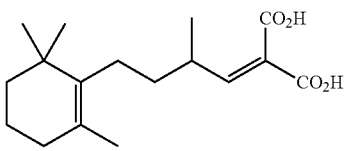 [SMILES: CC1=C(CCC(C)C=C(C(=O)O)C(=O)O)C(C)(C)CCC1]

Dimethyl malonate 3a (10 g, 28 mmol), TEBAC (0.33 g, 1.4 mmol) (or 18-Crown 6) and 1N NaOH (120 ml) are stirred at 100° C. for 3 days. Cooled to 25° C. the mixture is extracted with tert-butyl methyl ether and the organic phase, which contains aldehyde 5, is discarded. 100 ml 2 N HCl are added to the aqueous phase, which is extracted with tert-butyl methyl ether. The organic phase is washed with water, dried over MgSO$_4$, filtered and evaporated to give 7.15 g of crude bis-acid 1c (87%). Analytical data: $^1$H-NMR (400 MHz, CDCl$_3$): δ 0.96 (s, 6H), 1.13 (d, 3H), 1.35-1.6 (6H), 1.56 (s, 3H), 1.85-2.1 (4H), 3.5 (m, 1H), 7.6 (d, 1H) ppm. $^{13}$C-NMR (400 MHz, CDCl$_3$): δ 19.1 (q), 19.4 (t), 19.8 (q), 26.5 (t), 28.5 (2 q), 32.7 (t), 34.8 (s), 35.6 (d), 36.9 (t), 39.7 (t), 120.0 (s), 127.3 (s), 136.8 (s), 168.3 (s), 169.2 (d), 1669.7 (s). MS (DIP, EI): m/z (%) 294 (M$^+$, 67), 279 (8), 276 (14), 261 (18), 258 (17), 243 (100), 233 (12), 215 (22), 190 (16), 187 (15), 175 (32), 151 (14), 144 (44), 135 (32), 126 (14), 123 (31), 121 (16), 107 (9), 95 (9). IR (film): 2969 (m), 2929 (m), 2867 (m), 1701 (s), 1367 (m), 1262 (m), 1237 (m), 1199 (s), 1172 (m), 1067 (m), 842 (m), 761 (m).

EXAMPLE 8

Alternative preparation of 1c from aldehyde 5 by condensation with malonic acid: Aldehyde 5 (50 g, 0.24 mol), malonic acid (31 g, 0.3 mol), and piperidine (1 g, 12 mmol) in 100 ml iso-propanol are heated to 95° C. The iso-propanol/water azeotrope is continuously distilled off at 80° C. and replaced with dry iso-propanol. After 7 h the solvent is stripped off under reduced pressure. The residue is dissolved in cyclohexane and washed with 2 M aqueous HCl. The organic phase is concentrated under reduced pressure to give 75 of a viscous residue, which is dissolved in hexane (400 ml), heated to reflux and slowly cooled to 25° C. The precipitate is filtered, washed with cold hexane and dried to give 31.5 g (45%) of 1c in form of white crystals. Mp 110° C. The analytical data are identical to the ones obtained for this compound in example 7.

EXAMPLE 9

(E)-Methyl 4-methyl-6-(2,6,6-trimethylcyclohex-1-enyl)hex-3-enoate 4a

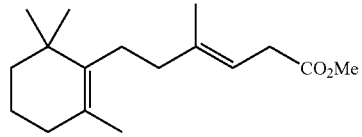 [SMILES: COC(=O)C/C=C(\C)CCC1=C(C)CCCC1(C)C]

Conjugated malonate 3a (0.5 g, 1.5 mmol), anhydrous lithium chloride (93 mg, 2.2 mmol) and water (53 mg, 3 mmol) in N-methyl-pyrrolidone (2.9 g, 29 mmol) are heated under stirring to 130° C. After 4 h at this temperature the mixture is poured upon 2 M HCl and extracted with tert-butyl methyl ether. The combined organic layers are washed with conc. $NaHCO_3$, conc. NaCl and dried over $MgSO_4$. After filtration and evaporation of the solvent the crude product (0.64 g) is bulb-to-bulb-distilled to give 0.4 g of 4a at 120° C./0.1 mbar. E/Z ratio 82:18. Analytical data of the E-isomer: $^1$H-NMR (400 MHz, $CDCl_3$): δ 1.0 (s, 6H), 1.4 (m, 2H), 1.55 (m, 2H), 1.6 (s, 3H), 1.7 (s, 3H), 1.9 (m, 2H), 2.1 (4H), 3.05 (d, 2H), 3.7 (s, 3H), 5.35 (t, 1H) ppm. $^{13}$C-NMR (400 MHz, $CDCl_3$): δ 16.35 (t), 19.5 (t), 19.8 (q), 27.5 (t), 28.6 (q, 2 C), 32.8 (t), 33.5 (t), 34.95 (s), 39.8 (t), 40.0 (t), 51.6 (q), 115.0 (d), 127.1 (s), 136.9 (s), 139.9 (s), 172.9 (s). MS (EI): m/z (%) 264 ($M^+$, 4), 249 ($[M-15]^+$, 1), 190 (3), 175 (3), 138 (10), 137 (100), 136 (21), 121 (12), 106 (11), 95 (73), 81 (45), 55 (19), 41 (21). Retention times (GC): 9.47 (Z), 9.56 (α,β), 9.62 (E) min. The mass spectra of the E- and Z-isomers are identical. IR (film): 2972 (m), 2865 (m), 1738 (s), 1434 (m), 1258 (m), 1199 (m), 1148 (m).

EXAMPLE 10

Alternative preparation of E-Cyclohomofarnesyl ester 4a by decarboxylation of 1b in the GC column: Half-malonate 1b is dissolved at 0.1% in tert-butyl methyl ether and is injected. Temperature program: 50° C./2 min, 20° C./min→200° C., 35° C./min→270° C. GC/MS: Agilent 5973 MSD with HP 6890 Series GC system. Non-polar column: BPX5 from SGE, 5% phenyl 95% dimethylpolysiloxan 0.2 mm×0.25 μm×12 m. Carrier Gas: Helium. Injector temperature: 230° C. Split 1:50. Flow: 1.0 ml/min. Transfer line: 250° C. MS-Quadrupol: 106° C. MS-Source: 230° C. Retention times: 9.48 (15%, Z-4a), 9.63 (57%, E-4a), 9.87 (12%, α,β-isomer). The mass-spectra of Z-4a and E-4a are identical. The analytical data are identical to the ones obtained for the E/Z mixture in example 9.

EXAMPLE 11

Alternative preparation of E-Cyclohomofarnesyl ester 4a by decarboxylation of 1a in DMSO: The NMR-tube containing the solution of 1a in $DMSO-D_6$, as prepared in Example 3 for NMR-analysis, is left at 25° C. as such. Repeated NMR-analysis after 3 days shows complete decarboxylation to 4a (E/Z ratio 78:22). The other analytical data are identical with the ones obtained for the E/Z mixture from example 9.

EXAMPLE 12

(E)-4-methyl-6-(2,6,6-trimethylcyclohex-1-enyl)hex-3-enoic acid 6: decarboxylation of 1c in the presence of LiCl

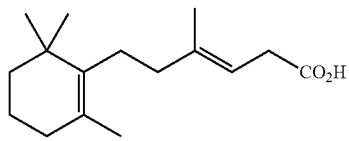 [SMILES: CC1=C(CC/C(C)=C/CC(=O)O)C(C)(C)CCC1]

Conjugated malonic acid 1c (2 g, 6.7 mmol) and anhydrous lithium chloride (0.3 g, 6.7 mmol) in N-methyl-pyrrolidone (4.5 g, 45 mmol) are heated under stirring to 100° C. After 2 h at this temperature the mixture is poured at 25° C. upon 2 M HCl and extracted with tert-butyl methyl ether. The combined organic layers are washed with water, conc. $NaHCO_3$ and conc. NaCl and dried over $MgSO_4$. Filtration and evaporation of the solvent under vacuum gives 1.9 g of crude 6 (quant). E/Z ratio 86:14 ($^{13}$C-NMR). The analytical data of 6 are identical to the ones described for this compound in EP 550889 (Kuraray, 1991).

EXAMPLE 13

Conjugated malonic acid 1c (3 g, 10 mmol) and 1-ethyl-3-methylimidazolium chloride (EMIMCl) (1.5 g, 10 mmol) in N-methyl-pyrrolidone (6.6 g, 66 mmol) are heated under stirring and nitrogen to 100° C. After 5 h at this temperature the mixture is poured at 25° C. upon 2 M HCl and extracted with tert-butyl methyl ether. The combined organic layers are washed with 2 M HCl, water and conc. $NaHCO_3$ and are dried over $MgSO_4$. Filtration and evaporation of the solvent under vacuum gives 2.6 g of crude 6 (quant). E/Z ratio 83:17 ($^{13}$C-NMR). The analytical data of 6 are identical to the ones described for this compound in EP 550889 (Kuraray, 1991).

EXAMPLE 14

One-pot-preparation of acid 6 from Aldehyde 5 catalyzed by ammonium acetate:

Under stirring and nitrogen aldehyde 5 (104 g, 0.5 mol), ammonium acetate (3.85 g, 50 mmol) and malonic acid (62.4 g, 0.6 mol) are heated in cyclohexane (250 ml) and tert-butanol (25 ml) to reflux (78° C.). After 2 h 5.5 ml water are collected in the Dean-Stark trap and after 4 h complete conversion is checked by TLC (system as above). 210 ml cyclohexane are distilled under reduced pressure (350 mbar). Magnesium chloride (24 g) in N-methyl-pyrrolidine (100 ml) are added within 5 min. After 5 h at 75° C. complete conversion of intermediate 1c to monoacid 6 is detected by TLC (system as above). The reaction mixture is cooled to 25° C. and poured upon water (400 ml). Extraction with hexane, washing of the combined organic layers with water, drying over MgSO4, filtration and evaportion of the combined organic phases under reduced pressure gives 123 g of an oily residue residue, which slowly solidifies upon standing. Purity=61% (E), according to $^1$H-NMR with internal standard dioxane. Yield: 56% based on aldehyde 5 and corrected by purity. Ratio E/Z/conj=85:8:7 ($^{13}$C-NMR in CDCl$_3$). The other analytical data of acid 6 obtained by this method are identical with the ones obtained for this compound (examples 12, 15, 16 and literature).

EXAMPLE 15

One-pot-preparation of acid 6 from Aldehyde 5 catalyzed by proline:

Under stirring and nitrogen aldehyde 5 (50 g, 0.24 mol), L-proline (2.8 g, 24 mmol) and malonic acid (31 g, 0.3 mol) are heated in cyclohexane (60 ml) and tert-butanol (40 ml) to reflux (80-85° C.). The cyclohexane/tert-butanol/water azeotropes are continuously distilled off and replaced with dry cyclohexane/tert-butanol. After 3 h complete conversion to bisacid 1c is detected by TLC. 60 ml of cyclohexane/tert-butanol/water azeotrope are distilled off at 80-85° C. Water-free Magnesium chloride (11.5 g, 0.12 mol) in dry N-methyl-pyrrolidinone (157 g, 1.55 mol) is added and the mixture heated for another 3 hours at 80-85° C. The solution is cooled to 25° C. and poured upon 2N aqueous HCl. Extraction with cyclohexane, washing of the organic phase with aqueous 2N HCl, extraction of the combined aqueous layers with cyclohexane and evaportion of the combined organic phases under reduced pressure gives a residue, which is further dried with cyclohexane under reduced pressure giving 63 g of a yellow oil with a purity of 79.5% (E+Z, determined by $^1$H-NMR with internal standard dioxane). E/Z ratio: 90:10 (according to $^{13}$C-NMR). The crude product is dissolved in hexane and slowly cooled to −20° C. The precipitate is filtered, washed with cold hexane to give 39.5 g of pure E-acid 6 (66% from aldehyde 5). Purity=96%, according to $^1$H-NMR with internal standard dioxane. Mp=49° C. The other analytical data of acid 6 obtained by this method are identical with the ones obtained for this compound (examples 12, 14, 16 and literature).

EXAMPLE 16

One-pot-preparation of acid 6 from Aldehyde 5 catalyzed by glycinyl glycine:

Prepared as described in example 14 from aldehyde 5 (50 g, 0.24 mol), H-Gly-Gly-OH (3.2 g, 24 mmol), malonic acid (31 g, 0.3 mol), magnesium chloride (11.5 g, 0.12 mol) in dry N-methyl-pyrrolidinone (71 g, 0.71 mol) using the same amount of solvents cyclohexane and t-Butanol within 3 h (for condensation) and 4 h (for decarboxylation). Work-up gave 70 g of crude 6 with a purity of 70% (E+Z, determined by $^1$H-NMR with internal standard dioxane). E/Z ratio: 90:10 (according to $^{13}$C-NMR). Yield: 74% (corrected and based on the E-isomer). The other analytical data of acid 6 obtained by this method are identical with the ones obtained for this compound (examples 12, 14, 15 and literature).

The invention claimed is:

1. A method for the preparation of an acid of formula 6,

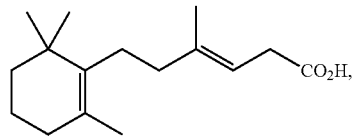

comprising decarboxylating the compound of formula 1

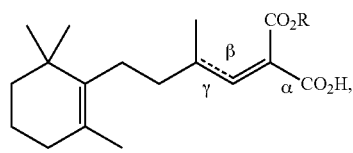

wherein R is hydrogen, in the presence of an inorganic salt or an organic cation/halide anion pair of the formula MX$_n$ at a temperature of 50 to 250 degrees centigrade, and in a polar aprotic solvent, wherein X is a halide and n is an integer of 1 to 3, and M is a group I, II or III metal when MX$_n$ is an inorganic salt, or M is selected from the group consisting of pyridinium, piperidinium, pyrrolidinium, imidazolium, ammonium, phophonium and sulphonium, when MX$_n$ is an organic cation/halide anion pair.

2. The method according to claim 1 wherein the metal salt is LiCl and/or MgCl$_2$ and the solvent is NMP.

* * * * *